(12) United States Patent
Wu

(10) Patent No.: US 9,603,687 B2
(45) Date of Patent: Mar. 28, 2017

(54) ORAL CARE IMPLEMENT

(75) Inventor: Donghui Wu, Bridgewater, NJ (US)

(73) Assignee: COLGATE-PALMOLIVE COMPANY, New York, NY (US)

(*) Notice: Subject to any disclaimer, the term of this patent is extended or adjusted under 35 U.S.C. 154(b) by 309 days.

(21) Appl. No.: 14/367,869

(22) PCT Filed: Dec. 21, 2011

(86) PCT No.: PCT/US2011/066594
§ 371 (c)(1),
(2), (4) Date: Jun. 20, 2014

(87) PCT Pub. No.: WO2013/095462
PCT Pub. Date: Jun. 27, 2013

(65) Prior Publication Data
US 2014/0352088 A1    Dec. 4, 2014

(51) Int. Cl.
| | |
|---|---|
| *A61C 17/28* | (2006.01) |
| *A61C 17/36* | (2006.01) |
| *A46B 13/04* | (2006.01) |
| *A61C 17/22* | (2006.01) |
| *A46B 11/00* | (2006.01) |

(Continued)

(52) U.S. Cl.
CPC ........ *A61C 17/227* (2013.01); *A46B 11/0051* (2013.01); *A46B 13/04* (2013.01); *A46B 15/0008* (2013.01); *A61C 17/28* (2013.01); *A61C 17/34* (2013.01); *A61C 17/3409* (2013.01); *A61C 17/3436* (2013.01); *A61C 17/36* (2013.01)

(58) Field of Classification Search
CPC ....... A46B 13/04; A61C 17/22; A61C 17/227; A61C 17/28; A61C 17/36
USPC ............... 15/22.1, 22.2, 22.4, 23, 24, 28, 29
See application file for complete search history.

(56) References Cited

U.S. PATENT DOCUMENTS

| | | |
|---|---|---|
| 818,000 A | 4/1906 | Stevenson |
| 1,711,755 A | 5/1929 | Smith |
| 3,661,018 A | 5/1972 | Keefer et al. |

(Continued)

FOREIGN PATENT DOCUMENTS

| | | |
|---|---|---|
| DE | 1802838 | 6/1969 |
| DE | 2735427 | 2/1979 |

(Continued)

OTHER PUBLICATIONS

Partial machine translation of DE 19935067, Feb. 8, 2001.*

(Continued)

*Primary Examiner* — Mark Spisich

(57) ABSTRACT

Provided is an oral care implement (1), comprising: a body (100); a carrier (130) connected to the body (100) and movable relative to the body (100), the carrier carrying one or more cleaning elements (134); a carrier drive mechanism (200) operable to drive movement of the carrier (130) relative to the body (100); an auxiliary device (400); and an auxiliary device drive mechanism (600) that is selectively engagable with the carrier drive mechanism (200) during operation of the carrier drive mechanism, so as to selectively operate the auxiliary device (400) during movement of the carrier (130) relative to the body (100). Also provided is a method of operating the oral care implement (1), and a kit of parts for an oral care implement.

25 Claims, 6 Drawing Sheets

(51) Int. Cl.
*A46B 15/00* (2006.01)
*A61C 17/34* (2006.01)

(56) References Cited

U.S. PATENT DOCUMENTS

| | | | | |
|---|---|---|---|---|
| 3,977,084 A * | 8/1976 | Sloan | ............... | A61C 17/005 |
| | | | | 15/29 |
| 4,146,020 A | 3/1979 | Moret et al. | | |
| 4,710,995 A | 12/1987 | Joyashiki et al. | | |
| 4,826,341 A | 5/1989 | Kwak | | |
| 5,142,723 A | 9/1992 | Lustig et al. | | |
| 5,301,381 A * | 4/1994 | Klupt | ............... | A46B 11/06 |
| | | | | 15/22.1 |
| 5,458,563 A * | 10/1995 | Stewart | ............ | A46B 11/063 |
| | | | | 15/24 |
| 6,047,429 A | 4/2000 | Wu | | |
| 6,095,964 A | 8/2000 | Purvey | | |
| 6,164,967 A * | 12/2000 | Sale | ............... | A46B 11/002 |
| | | | | 15/22.1 |
| 6,325,076 B1 | 12/2001 | Ramirez | | |
| 7,059,853 B2 | 6/2006 | Hegemann | | |
| 7,069,552 B2 | 6/2006 | Lindberg et al. | | |
| 7,080,980 B2 * | 7/2006 | Klupt | ............... | A61C 17/222 |
| | | | | 15/167.1 |
| 7,972,136 B2 | 7/2011 | Hegemann | | |
| 8,522,384 B2 * | 9/2013 | Leung | ............... | A61C 17/36 |
| | | | | 15/29 |
| 8,539,630 B2 | 9/2013 | Gatzemeyer et al. | | |
| 2005/0004498 A1 | 1/2005 | Klupt | | |
| 2005/0066996 A1* | 3/2005 | France | ............... | A46B 9/028 |
| | | | | 134/6 |
| 2005/0238412 A1 | 10/2005 | Jacobs et al. | | |
| 2005/0271531 A1 | 12/2005 | Brown et al. | | |
| 2006/0078844 A1* | 4/2006 | Goldman | ............ | A61C 1/0084 |
| | | | | 433/80 |
| 2010/0186179 A1* | 7/2010 | Miller | ............... | A61C 1/07 |
| | | | | 15/22.2 |
| 2010/0278582 A1 | 11/2010 | Boland et al. | | |
| 2010/0284728 A1 | 11/2010 | Heil et al. | | |
| 2011/0219623 A1 | 9/2011 | Rockell et al. | | |
| 2011/0262879 A1 | 10/2011 | Hegemann et al. | | |

FOREIGN PATENT DOCUMENTS

| | | | |
|---|---|---|---|
| DE | 3416874 | | 11/1985 |
| DE | 9107226 | | 8/1991 |
| DE | 19935067 | * | 2/2001 |
| DE | 102005045226 | | 3/2007 |
| FR | 2290129 | | 5/1976 |
| FR | 2748914 | | 11/1977 |
| GB | 1264138 | | 2/1972 |
| JP | 2006-61486 | * | 3/2006 |
| WO | WO9856309 | | 12/1998 |
| WO | WO03101365 | | 12/2003 |

OTHER PUBLICATIONS

International Search Report and the Written Opinion issued in International Application PCT/US2011/066594 mailed Mar. 25, 2013.

Written Opinion of the International Preliminary Examining Authority issued in International Application PCT/US2011/066594 mailed Mar. 25, 2013.

* cited by examiner

ORAL CARE IMPLEMENT

CROSS-REFERENCE TO RELATED APPLICATIONS

This application is a U.S. national stage application under 35 U.S.C. §371 of PCT Application No. PCT/US2011/066594, filed Dec. 21, 2011, the entirety of which is incorporated herein by reference.

FIELD OF THE INVENTION

The present invention relates to an oral care implement, and more particularly to an oral care implement such as a toothbrush that has an auxiliary device and a mechanism for operating the auxiliary device. The auxiliary device may be a pump for pumping a fluid from an outlet of the implement.

BACKGROUND OF THE INVENTION

Oral care implements such as toothbrushes are typically used in conjunction with a dentifrice or similar oral care product for cleansing the teeth and/or soft tissue in the oral cavity. The dentifrice or product may contain one or more ingredients which, when administered with the oral care implement generally via a brushing or rubbing action, provide an oral health benefit to the user, such as removing plaque and debris from the surface of the teeth and/or gums, polishing and whitening teeth, reducing sensitivity, reducing oral surface bacteria populations, and other benefits. However, it is often advantageous when brushing one's teeth or rubbing soft tissue in one's oral cavity to supplement the oral care benefit(s) by further dispensing one or more additional oral care products in a fluid form into the oral cavity, or by further stimulating the soft tissue, in order to optimize the oral care regimen.

US2010/278582 and US2005/238412 disclose respective electric toothbrushes, each with two motors. One of the motors is for driving movement of a brush head, while the other of the motors is for driving a pump. U.S. Pat. No. 5,142,723 describes a toothbrush with a motor that concurrently drives both a brush head and a pump. US2010/0284728 discloses an electric toothbrush with a moveable brush head, a pump for pumping fluid to the brush head, and a motor. Rotation of the motor in either direction drives movement of the brush head, and the pump is driven only in one rotation direction of the motor.

Each of these prior art toothbrushes has inherent problems, such as being bulky and/or heavy, wasteful of oral care fluid, or inconvenient to use.

An improved oral care implement, such as a toothbrush, capable of dispensing a fluid while in the oral cavity, or stimulating soft tissue, is therefore desired.

SUMMARY OF THE INVENTION

A first aspect of the present invention may provide an oral care implement, such as a toothbrush, comprising: a body; a carrier connected to the body and movable relative to the body, the carrier carrying one or more cleaning elements; a carrier drive mechanism operable to drive movement of the carrier relative to the body; an auxiliary device; and an auxiliary device drive mechanism that is selectively engagable with the carrier drive mechanism during operation of the carrier drive mechanism, so as to selectively operate the auxiliary device during movement of the carrier relative to the body.

Preferably, the auxiliary device drive mechanism is selectively engagable with the carrier drive mechanism through relative movement of at least part of the auxiliary device drive mechanism and at least part of the carrier drive mechanism. More preferably, the auxiliary device drive mechanism is selectively engagable with the carrier drive mechanism through movement of at least part of the auxiliary device drive mechanism relative to the body and relative to at least part of the carrier drive mechanism. Preferably the oral care implement comprises a clutch that is operable by a user to selectively engage the auxiliary device drive mechanism with the carrier drive mechanism.

Optionally, the carrier drive mechanism comprises a first movable part and the auxiliary device drive mechanism comprises a second movable part, wherein the operation of the carrier drive mechanism causes movement of the first movable part, and wherein the second moveable part is selectively engagable with the first movable part during the movement of the first movable part.

The first movable part may be a first rotatable part and the movement of the first movable part comprises rotation of the first rotatable part.

The second movable part may be a second rotatable part. Preferably the first rotatable part is rotatable about a first axis and the second rotatable part is rotatable about a second axis.

The second rotatable part may be selectively engagable with the first rotatable part by changing a distance between the first axis and the second axis. For example, the second rotatable part may be selectively engagable with the first rotatable part by reducing a distance between the first axis and the second axis.

The first axis may be parallel to the second axis or non-parallel, such as perpendicular, to the second axis.

The first and second axes may be coaxial, in which case the first rotatable part may be selectively engagable with the first rotatable part by changing a distance between the first and second rotatable parts in a direction parallel to the axes.

Preferably the first rotatable part comprises a first gear and the second rotatable part comprises a second gear.

Optionally, one of the first movable part and the second movable part comprises a rotatable element and the other of the first movable part and the second movable part comprises an elongate flexible element. The rotatable element may comprise one of a pulley and a toothed wheel, and the elongate flexible element may comprise one of a belt, a chain, a wire and a cable.

Preferably the auxiliary device drive mechanism is biased out of engagement with the carrier drive mechanism.

Preferably the oral care implement comprises a selector that is operable by a user to cause the auxiliary device drive mechanism to engage with the carrier drive mechanism. The selector may be movable between first and second positions. Preferably the selector is biased to the first position, wherein, when the selector is in the first position, the auxiliary device drive mechanism is disengaged from the carrier drive mechanism, and, when the selector is in the second position, the auxiliary device drive mechanism is engaged with the carrier drive mechanism.

The oral care implement may comprise an electromagnet and a metallic or ferromagnetic member, wherein when the electromagnet is energized, the electromagnet and the member move relative to one another to cause the auxiliary device drive mechanism to engage with the carrier drive mechanism.

The oral care implement may comprise a timer configured to measure a predetermined period of time from engagement of the auxiliary device drive mechanism with the carrier drive mechanism, wherein the implement is configured such that, when the timer has measured elapse of the predetermined period of time, the auxiliary device drive mechanism is disengaged from the carrier drive mechanism.

Preferably the auxiliary device comprises a pump, preferably a peristaltic pump, and more preferably a rotary peristaltic pump.

The oral care implement may comprise a reservoir for holding a fluid, one or more outlets formed in a surface of the body, and a fluid flow channel that links the reservoir to the one or more outlets, wherein the pump is operable to pump fluid from the reservoir to the one or more outlets via the fluid flow channel.

Preferably, the pump comprises a peristaltic pump and the fluid flow channel comprises a compressible tube, a first portion of the tube being compressed between two components of the peristaltic pump, wherein operation of the peristaltic pump comprises movement of at least one of the two components relative to the first portion of the tube, such that compression of the first portion of the tube is relaxed and such that a second, different portion of the tube, which second portion is closer than the first portion of the tube to the one or more outlets, becomes compressed between two components, whereby fluid is pumpable along the tube towards the one or more outlets. Preferably the peristaltic pump comprises a rotary peristaltic pump in which at least one of the two components is rotatable about an axis.

Optionally, the carrier drive mechanism comprises a motor and one or more elements coupling the motor to the carrier, wherein rotation of an output shaft of the motor drives movement of the carrier relative to the body. The oral care implement may comprise one or more batteries electrically connected to the motor. Preferably the body comprises a housing and the reservoir is located in a space between an outer wall of the housing and one of the one or more batteries.

A second aspect of the present invention may provide a kit of parts for an oral care implement, such as a toothbrush, the kit of parts comprising: a handle; and a head connectable to the handle, the head comprising a carrier that is movable relative to the handle when the head is connected to the handle, the carrier carrying one or more cleaning elements; wherein the handle comprises: a carrier drive mechanism operable to drive movement of the carrier relative to the handle when the head is connected to the handle; an auxiliary device; and an auxiliary device drive mechanism that is selectively connectable to the carrier drive mechanism during operation of the carrier drive mechanism, so as to selectively operate the auxiliary device during movement of the carrier relative to the handle.

A third aspect of the present invention may provide a method of operating an oral care implement, such as a toothbrush, which oral care implement comprises a body; a carrier connected to the body and movable relative to the body, the carrier carrying one or more cleaning elements; a carrier drive mechanism operable to drive movement of the carrier relative to the body; an auxiliary device; and an auxiliary device drive mechanism that is selectively engagable with the carrier drive mechanism during operation of the carrier drive mechanism, so as to selectively operate the auxiliary device during movement of the carrier relative to the body; wherein the method comprises: operating the carrier drive mechanism to drive movement of the carrier relative to the body; and selectively connecting the auxiliary device drive mechanism to the carrier drive mechanism during operation of the carrier drive mechanism, so as to selectively operate the auxiliary device during movement of the carrier relative to the body.

A fourth aspect of the present invention may provide an oral care implement, comprising: a body, one or more outlets being formed in a surface of the body; a rotary peristaltic pump being disposed within the body; and a fluid flow channel that links the pump to the one or more outlets, wherein the pump is operable to pump fluid to the one or more outlets via the fluid flow channel; wherein the fluid flow channel comprises a compressible tube; wherein the pump comprises a rotor and a housing, a first portion of the compressible tube being compressed between the rotor and the housing; and wherein the rotor is rotatable about an axis that is in a fixed position relative to the body.

The oral care implement of the fourth aspect may comprise a carrier connected to the body and movable relative to the body, the carrier carrying one or more cleaning elements; a carrier drive mechanism operable to drive movement of the carrier relative to the body; and a pump drive mechanism that is engaged with the carrier drive mechanism, so as to operate the pump during movement of the carrier relative to the body. Preferably, the pump drive mechanism is selectively engagable with the carrier drive mechanism during operation of the carrier drive mechanism, so as to selectively operate the pump during movement of the carrier relative to the body.

A fifth aspect of the present invention may provide a kit of parts for an oral care implement, the kit of parts comprising: a handle; and a head connectable to the handle, wherein the head comprises one or more cleaning elements and a first fluid flow channel, wherein one or more outlets are formed in a surface of the head, and the first fluid flow channel is in fluid communication with the one or more outlets; wherein the handle comprises a housing, within which are disposed: a rotary peristaltic pump; and a second fluid flow channel that engages the first fluid flow channel when the head is connected to the handle so as to link the pump to the one or more outlets when the head is connected to the handle, whereby the pump is operable to pump fluid to the one or more outlets via the first and second fluid flow channels; wherein the second fluid flow channel comprises a compressible tube; wherein the pump comprises a rotor and a housing, a first portion of the compressible tube being compressed between the rotor and the housing; and wherein the rotor is rotatable about an axis that is in a fixed position relative to the housing of the handle.

In the kit of parts of the fifth aspect, preferably the head comprises a carrier that is movable relative to the handle when the head is connected to the handle, the carrier carrying the one or more cleaning elements. Preferably the handle comprises a carrier drive mechanism that is operable to drive movement of the carrier relative to the handle when the head is connected to the handle, and a pump drive mechanism that is engaged with the carrier drive mechanism so that the pump is operated during movement of the carrier relative to the handle.

DETAILED DESCRIPTION OF THE PREFERRED EMBODIMENTS

Figure 1:
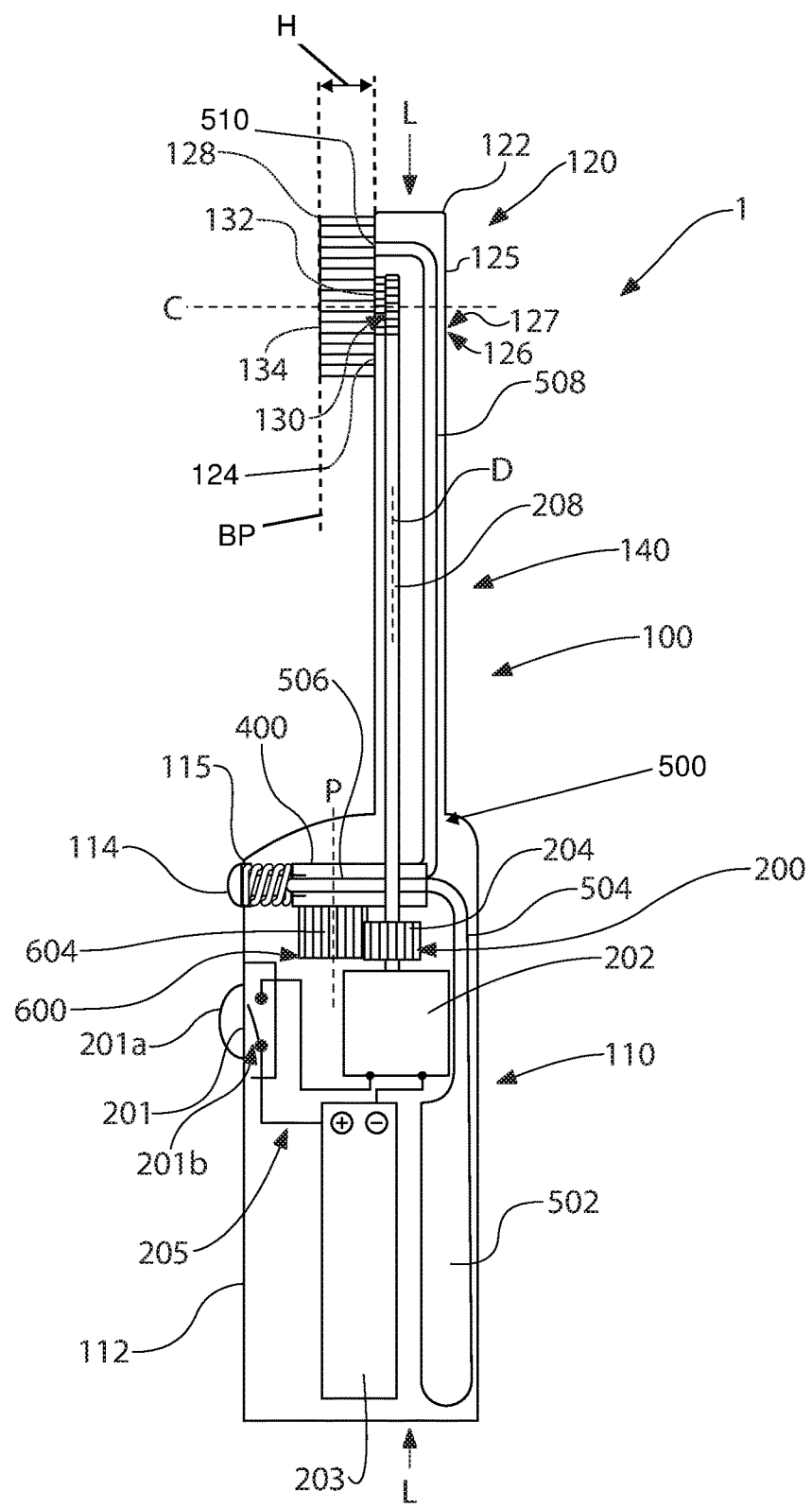
FIG. 1 is a longitudinal cross sectional view of an oral care implement according to a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combination of features that may exist alone or in other combinations of features; the scope of the invention being defined by the claims appended hereto.

In the following description, the invention is discussed in terms of a toothbrush, but could be in the form of another oral care implement, such as a tissue cleansing implement. The oral care implement is preferably self-contained, portable and hand-held. Further, it is understood that other embodiments may be utilized and structural and functional modifications may be made without departing from the scope of the present invention, as defined by the claims.

FIG. 1 illustrates a toothbrush according to an embodiment of the present invention, generally designated with the reference numeral 1. The toothbrush 1 generally comprises a body 100 that comprises a handle 110, a head 120, and a neck 140 that connects the handle 110 to the head 120. The head 120 is that part of the toothbrush 1 that is intended to be inserted into a user's mouth during use, although in practice at least part of the neck 140 may also be inserted into the user's mouth during use. The toothbrush 1 has a longitudinal axis L, which may also be considered a longitudinal axis L of the head 120 and the neck 140.

The head 120 comprises a support 122 and a carrier 130, each of which may be made of a rigid material, such as polypropylene. The support 122 has a front brushing side or surface 124, an opposing back side or surface 125, and two opposing lateral sides 126, 127 that join the front and back sides or surfaces 124, 125. A distance between the lateral sides 126, 127 defines a width of the head 120. The shape of the front and back surfaces 124 and 125 respectively may be generally planar/flat, curved, or any combination thereof. The front brushing surface 124 is preferably substantially parallel to the longitudinal axis L of the head 120.

The carrier 130 is connected to the support 122 and is movable relative to the support 122 and thus relative to the body 100 of the toothbrush 1. In this embodiment, the carrier 130 is rotatable relative to the support 122 about an axis C that is substantially perpendicular to the longitudinal axis L of the head 120 and that is substantially perpendicular to the width of the head 120. In embodiments in which the front brushing surface 124 is planar, the axis C is preferably normal to the plane in which the front brushing surface 124 lies.

The carrier 130 carries one or more cleaning elements 134. The cleaning elements 134 extend from a front face 132 of the carrier 130, which front face 132 faces in the same direction as the front brushing surface 124 of the support 122. The front face 132 of the carrier 130 and the front brushing surface 124 are preferably coplanar. The cleaning element(s) 134 preferably comprise tooth cleaning elements, but may instead or additionally comprise soft tissue cleaning elements. Such tooth cleaning elements may be connected to the carrier 130 by any suitable conventional attachment method used in the art including, without limitation, anchor free tufting (AFT) in mold tufting (IFT) and stapled/anchored. Tooth cleaning elements may include a variety of bristle and/or flexible elastomeric cleaning and/or polishing elements. It should be noted that the cleaning elements 134 in the drawings are illustrated substantially in block without the individual bristle strands being detailed for convenience and clarity so as to not obscure other structures on head 120. As shown in FIG. 1, cleaning elements 134 collectively define an overall maximum height H measured upwards and transverse to front face 132 of the carrier 130 and define an imaginary nominal reference brushing plane BP. Brushing plane BP is roughly defined by the upper free ends of the cleaning elements 134 (with lower fixed ends being attached to the front face 132) and is offset from the front face 132 (with some variation allowing for varying heights of some of the cleaning elements 134).

Any provided bristles are preferably made from nylon, although other materials could be used. The bristles also preferably have a generally circular cross-sectional shape, but could have other cross-sectional shapes as well. The diameter of the bristles can vary depending on the desired cleaning action of the bristles. Any provided soft tissue cleaning element(s) are preferably made from an elastomer, such as a thermoplastic elastomer (TPE), or rubber. The soft tissue cleaning element(s) may comprise one or more tissue engaging elements, such as elongated cleaning elements, which may be linear or nonlinear, and/or one or more nubs.

As used herein, a "nub" is generally meant to include a column-like protrusion (without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection), the base width can be substantially larger than the height.

The cleaning elements 134 carried by the carrier 130 may be arranged in any suitable pattern and the invention is not limited by any particular arrangement, shape, type, and/or number of cleaning element(s) 134 provided.

In some embodiments, any one or more of the front brushing surface 124 itself, the back surface 125, and the two opposing lateral sides 126, 127 of the head 120 may include an elastomeric tongue cleaner and/or other tooth or soft tissue cleaning elements (not shown), of any of the forms discussed above. For example, as shown in FIG. 1, a number of tooth cleaning elements 128 extend from the front brushing surface 124 and surround the carrier 130. The toothbrush head 120 may have an elongated elliptical or oval shape in top view; however, in other embodiments the head 120 may be round in top view.

The handle 110 is a member that is dimensioned so that a user can readily grip and manipulate the toothbrush 1. The handle 110 may have any suitable ergonomic and aesthetically pleasing configuration dimensioned to be gripped by a user, and is not limited to the appearance illustrated in the enclosed drawings.

The handle 110 comprises an outer shell or housing 112, which preferably is made of a relatively rigid plastic material, such as polypropylene. Within the housing 112 is housed a motor 202 and a pair of batteries 203. A user-operable switch 201, such as a toggle switch, is disposed on an outer side of the housing 112. The switch 201 is configured such that, when the switch 201 is operated by a user, the motor 202 becomes electrically connected to the batteries 203, so that the motor 202 becomes powered by the batteries 203 to cause rotation of an output shaft of the motor 202 relative to the housing 112. The switch 201 comprises a user-contactable surface 201a, which in this embodiment is a dome-shaped surface, and an electric switch 201b within the housing 112. The surface 201a and the electric switch 201b are relatively disposed such that, when a force is applied to the surface 201a by a user, the electric switch 201b is caused to change from an open state, in which an electric circuit 205 comprising the motor 202 and the batteries 203 is incomplete, to a closed state, in which the circuit 205 is complete and current flows through the motor 202.

The switch 201 need not be of the specific form illustrated in FIG. 1, but could take any form suitable to be operable by a user to cause operation of the motor 202.

Although in this embodiment only a pair of batteries 203 is provided, in other embodiments there may be provided more than two batteries 203 to which the motor 202 becomes electrically connected when the switch 201 is operated by a user, or only a single battery 203.

The output shaft of the motor 202 is connected to a first end of a drive element 208. In this embodiment, the drive element 208 comprises a drive shaft that is mounted within the toothbrush 1 so as to be rotatable about a longitudinal axis D of the drive element 208 relative to the body 100, which longitudinal axis D of the drive element 208 is substantially parallel to the longitudinal axis L of the toothbrush 1. A first end of the drive shaft 208 is located within the housing 112 of the handle 110, and the drive shaft 208 extends to within the support 122 of the head 120.

A second end of the drive shaft 208, which is located within the head 120, is connected to the carrier 130, in this embodiment by a pair of meshed gears (not shown). One of the gears is mounted on, or integral with, the drive shaft 208 and is rotatable about the longitudinal axis D of the drive shaft 208, and the other of the gears is mounted on, or integral with, the carrier 130 and is rotatable about the axis C of rotation of the carrier 130. The meshed gears may, for example, be a pair of meshed bevel gears or a worm and a wheel. The invention is not limited to the use of meshed gears to connect the carrier 130 and drive shaft 208, but instead encompasses any arrangement suitable and operable to connect the carrier 130 and drive shaft 208 such that movement of the drive shaft 208 relative to the body 100 translates into movement of the carrier 130 relative to the body 100.

While in the illustrated embodiment the drive element 208 acts on the carrier 130 to rotate the carrier 130 continuously (i.e. over an angle of more than 360°), in alternative embodiments the drive element 208 and the carrier 130 may be suitably connected such that movement of the drive element 208 drives the carrier 130 to oscillate the carrier 130 back and forth in two opposing rotational directions about its axis C of rotation over a total angle that is less than 360°. Such a suitable connection could comprise, for example, a bent end of the rotatable drive element 208 engaging a slot formed in the carrier 130, such that the bent end and the slot cooperate as a cam-and-follower mechanism. Moreover, the invention is not limited such that movement of the carrier 130 relative to the support 122 and the body 100 as a whole is necessarily rotational movement. In some embodiments, the drive element 208 drives the carrier 130 to translate the carrier 130 relative to the support 122 and the body 100. In alternative embodiments, the drive element 208 drives the carrier 130 to rock the carrier 130 relative to the support 122 and the body 100.

Mounted on, or integral with, another part of the drive shaft 208 that is closer to the motor 202 is a gear 204, which is referred to herein as a first gear 204. The first gear 204 rotates about the longitudinal axis D of the drive shaft 208 when the drive shaft 208 rotates. Together, the motor 202, the drive shaft 208 and the first gear 204 are herein referred to as an example of a "carrier drive mechanism" 200. Rotation of the output shaft of the motor 202 drives rotation of the drive shaft 208 (and the first gear 204), which in turn drives rotation of the carrier 130. That is, the carrier drive mechanism 200 is operable to drive movement, in this case rotation, of the carrier 130 relative to the body 100 of the toothbrush 1. The first gear 204 is referred to herein as a movable part of the carrier drive mechanism 200, and more particularly as a rotatable part of the carrier drive mechanism 200.

The toothbrush 1 also comprises an auxiliary device 400. In this embodiment, the auxiliary device 400 comprises a pump, and more specifically a positive displacement pump in the form of a peristaltic pump 400. The pump 400 in this embodiment is disposed within the housing 112 of the handle 110 and is described in more detail below.

The toothbrush 1 further comprises a fluid transport system 500. The fluid transport system 500 comprises a reservoir 502 holding, or for holding, a fluid, an outlet 510 formed in the front brushing surface 124 of the support 122 of the head 120, and a fluid flow channel that links the reservoir 502 to the outlet 510. The fluid flow channel comprises a first channel portion 504 in direct fluid communication with the reservoir 502 and disposed within the housing 112, a third channel portion 508 in direct fluid communication with the outlet 510 and disposed in the neck 140, and a second channel portion 506 fluidly connecting the first and third channel portions 504, 508. In this embodiment, each of the first and third channel portions 504, 508 are flexible tubes. In alternative embodiments, the first and third channel portions 504, 508 may be channels integrally formed with the housing 112 and the neck 140, respectively, during molding of the housing 112 and the neck 140. The peristaltic pump 400 is operable to pump fluid from the reservoir 502 to the outlet 510 via the fluid flow channel, as will be described in more detail below.

While in the illustrated embodiment the outlet 510 is formed in the front brushing surface 124 of the support 122, in other embodiments the outlet 510 may be formed elsewhere on the head 120, such as on one of the opposing back surface 125, and the two opposing lateral sides 126, 127. In some embodiments, a plurality of outlets 510 may be provided on the head 120, with each of the outlets 510 being in fluid communication with the third channel portion 508. In some embodiments, alternatively or additionally to the provision of one or more outlets 510 on the head 120, there may be provided one or more such outlets 510 elsewhere on the body 100 of the implement 1, such as on the neck 140.

Figure 5:
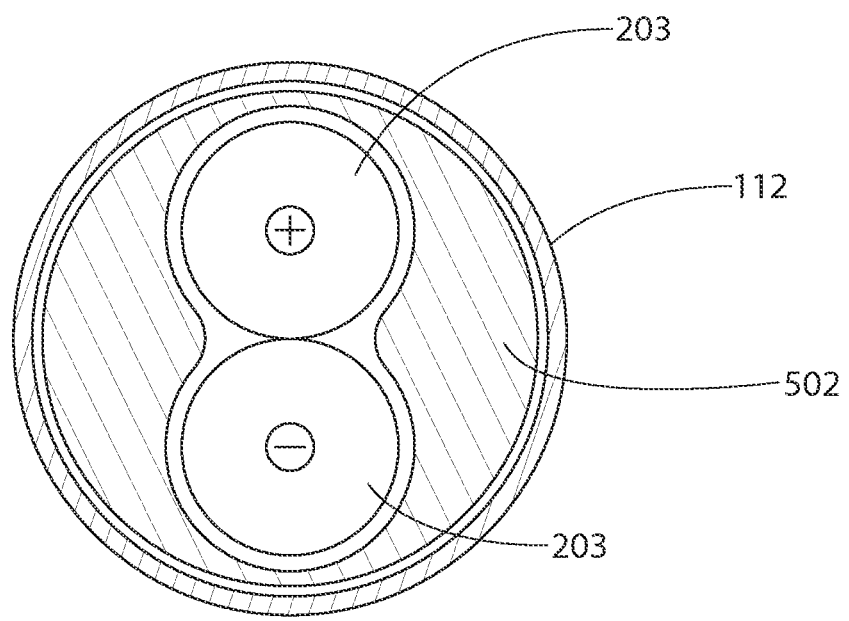
FIG. 5 is a lateral cross sectional view of the oral care implement of FIG. 1.

The reservoir 502 is made of a soft material, such as a thermally-sealable plastic film, and is configured to collapse to avoid negative pressure as fluid is pumped out of the reservoir 502 by the pump 400. The reservoir 502 could, for example, take the form of a collapsible bag, pouch or bellows. In any event, the reservoir 502 deforms as the quantity of fluid it contains decreases. The collapsible reservoir 502 is disposed within the housing 112 of the handle 110. More specifically, the reservoir 502 is disposed in a space between an outer wall of the housing 112 and one or more of the battery(ies) 203 that power the motor 202, as shown for example in FIG. 5. This space may be considered an irregularly-shaped space, yet the flexible nature of the material of the reservoir 502 is such that the reservoir 502 conforms to the available space between the housing 112 and the battery(ies) 203.

The reservoir 502 may be made of any suitable deformable and collapsible material. The selected material, however, should be compatible with the oral care agent or fluid that is to be stored within the reservoir 502 and preferably should not be corroded, embrittled, cracked, or otherwise degraded by the oral care agents or fluid during storage therein for a reasonable period of time.

The fluid held in the reservoir is preferably an oral care fluid. The fluid may contain one or more active or inactive oral care agents. The fluid may serve as a carrier mechanism for one or more active oral care agents, and/or may be of any suitable viscosity substance, ranging from preferably moderately viscous pastes/gels or less viscous liquid compositions to very viscous liquids, so long as the fluid may be transported from the reservoir 502, through the fluid flow channel, and dispensed from the outlet(s) 510 by the pump 400 described herein.

Any suitable active or inactive oral care agent can be used in embodiments of the present invention. For example, the oral care agent may include whitening agents, including without limitation, peroxide containing tooth whitening compositions. Suitable peroxide containing tooth whitening compositions are disclosed in U.S. patent Ser. No. 11/403, 372, filed Apr. 13, 2006, to the present assignee, the entirety of which is hereby incorporated by reference. While a tooth whitening agent is one agent that may be used in the present invention, any other suitable other oral agents can be used and stored within reservoir 502. Contemplated possible oral care agents include without limitation, antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. The oral care agent may comprise toothpaste. However, preferably the fluid is free of (i.e., is not) toothpaste. Instead, the oral care agent is intended to provide supplemental oral care benefits in addition to merely brushing one's teeth.

The reservoir 502 may be replaceable. The reservoir 502 may be removably attached to the first channel portion 504 via any suitable conventional non-permanent mechanical coupling means including without limitation a threaded connection, releasable frictional or snap fit, or other. In a preferred exemplary embodiment, a threaded connection is used, wherein the reservoir 502 is rotatably attached to the first channel portion 504. Accordingly, a distal coupling end of the reservoir 502 may include a neck having male threads which are rotatably coupled with a complementary female threaded socket disposed on the first channel portion 504. Any suitable threading configuration and pitch may be used so long as reservoir may be removably attached to the first channel portion 504. In other possible embodiments contemplated, the neck of the reservoir has a female threaded socket which rotatably couples with a male threaded neck on the first channel portion 504. Accordingly, the invention is not limited to either of the foregoing threaded constructions or other arrangements. The housing 112 of the handle 110 may include an opening, which may be covered and uncoverable by a door, through which a user is able to access the reservoir 502 to initially connect, or later replace, the reservoir 502.

In some embodiments, the reservoir 502 is refillable while connected to the first channel portion 504. In such embodiments, the reservoir may include a valve or an openable closure, through which fluid may be injected into the interior of the reservoir 502 from outside of the housing 112.

The possible forms and positions of the reservoir 502 discussed above are not limiting on the scope of the invention, unless otherwise stated in the claims.

Figure 2A:
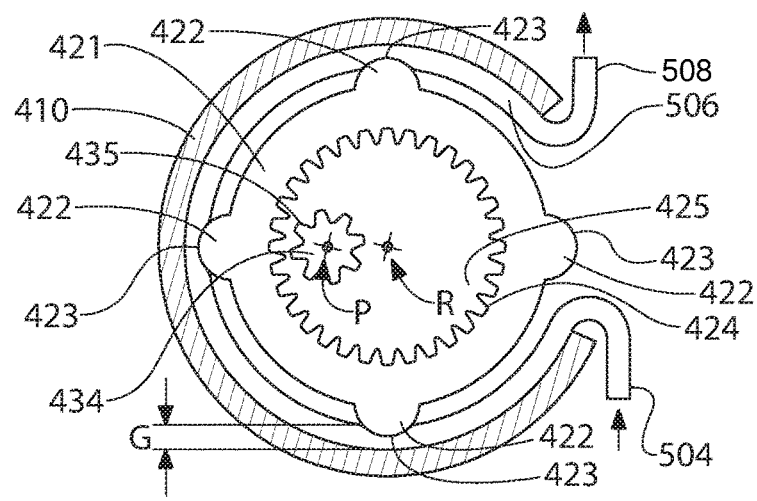
FIG. 2A is a cross sectional view of a pump of the oral care implement of FIG. 1.

In this embodiment, the pump 400 is a rotary peristaltic pump that takes the form shown in FIG. 2A. The pump 400 comprises two components, namely a pump housing 410 and a rotor 420, each of which is made of a rigid, or substantially rigid, material. Preferably the pump housing 410 and the rotor 420 are made of a material that is more rigid than the material from which the second channel portion 506 is made. The second channel portion 506 comprises an elastically-deformable compressible tube, while the pump housing 410 and the rotor 420 are preferably of a relatively hard material such as a plastics or metallic material.

The rotor 420 is disposed within the pump housing 410 and is mounted to the pump housing 410 for rotation about a rotor axis R relative to the compressible tube 506 and the pump housing 410. The rotor axis R is fixed relative to the pump housing 410 and is parallel to the longitudinal axis D of the drive shaft 208, i.e. the axis of rotation of the first gear 204.

The rotor 420 comprises a ring member 421 and four arms 422 extending radially from an external circumference of the ring member 421. A respective shoe or wiper 423 is disposed at the radial end of each of the arms 422. The compressible tube 506 is disposed between the pump housing 410 and the shoes 423 of the rotor 420. Measured in a radial direction from the axis R about which the rotor 420 rotates, a gap G between the pump housing 410 and the outer radial side of each of the shoes 423 is smaller than the diameter or width of the compressible tube 506 in the same direction. Accordingly, one or more portions of the compressible tube 506 are compressed (i.e. pinched) between the pump housing 410 and the rotor 420 at any one point in time. As the rotor 420 rotates relative to the compressible tube 506 and relative to the pump housing 410, compression of any one portion of the compressible tube 506 that is initially compressed by one of the shoes 423 is relaxed and a second portion of the compressible tube 506 becomes compressed. The second portion of the compressible tube 506 is closer to the third channel portion 508 than the first portion of the compressible tube 506, so fluid in the compressible tube 506 downstream from the compressed portion of the compressible tube 506 is pushed by the shoe 423 towards the third channel portion 508 and thus towards the outlet(s) 510. That is, as the rotor 420 rotates, a portion of the tube 506 occludes or closes, thus forcing the fluid through the tube 506. Additionally, as the compressive force on the portion of the tube 506 is relaxed and the portion of the tube 506 is allowed to recover to, or towards, its natural more open state after the passing of the shoe 423, flow of fluid is induced from the reservoir 502 to the compressible tube 506 via the first channel portion 504. Accordingly, the pump 400 acts to pump fluid from the reservoir 502 to the outlet(s) 510 by peristalsis.

It will be appreciated that the rate at which fluid is pumped by the pump 400 is proportional to each of: (a) the inner cross sectional area of the tube 506, (b) the diameter of the pump housing 410, and (c) the rotation speed of the rotor 420.

In the embodiment illustrated in FIG. 2A, the rotor 420 has four arms 422 and associated shoes 423 disposed at equal intervals around the circumference of the ring member 421. That is, the shoes 423 are circumferentially spaced 90° apart, such that the circumferential spacing between any two of the shoes 423 is equal to the circumferential spacing between any other two of the shoes 423. This equal spacing provides a regular and relatively smooth pumping action of fluid towards the outlet(s)510. In other embodiments, the spacings need not be equal. In some embodiments, the ring member 421 also includes an opening through which the drive element 208 extends. The opening in the ring member 421 is sufficiently large to allow for the rotation of the ring member 421 without interference or friction from the drive element 208 which extends from the motor 202 through the opening (not shown) and to the carrier 130.

Figure 2B:
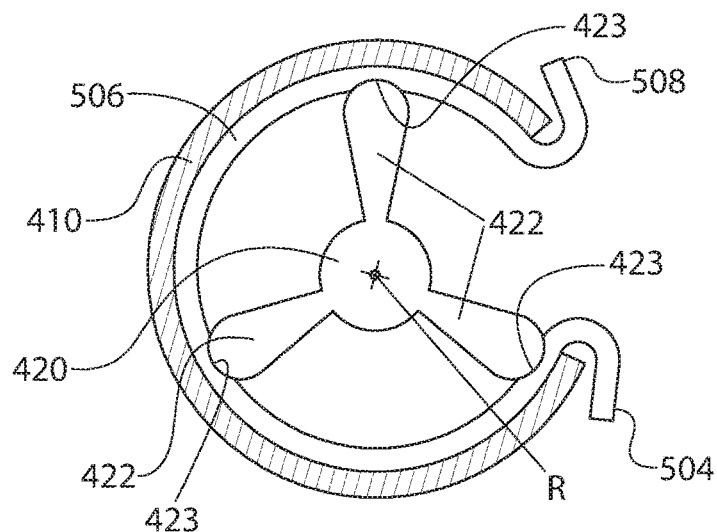
FIG. 2B is a cross sectional view of a pump of an oral care implement according to an alternative embodiment of the present invention.
Figure 2C:
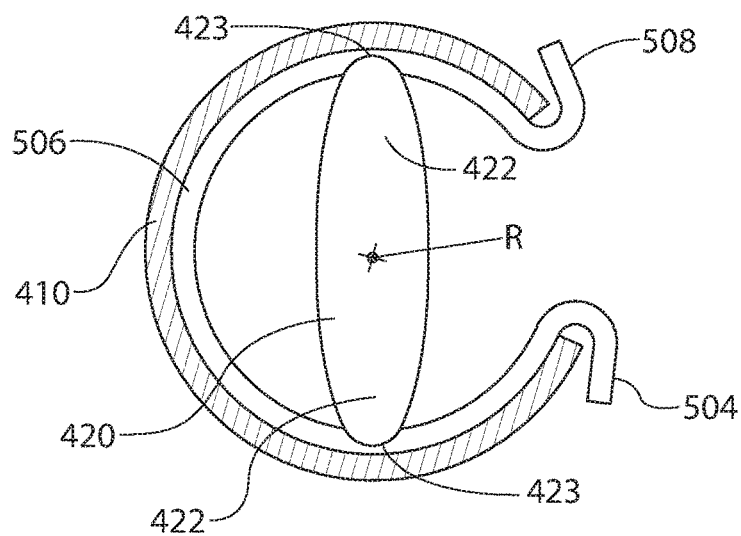
FIG. 2C is a cross sectional view of a pump of an oral care implement according to a further alternative embodiment of the present invention.

In the embodiment illustrated in FIG. 2A, the rotor 420 has four shoes 423. However, in other embodiments, the rotor 420 may have more or fewer shoes 423. For example, FIG. 2B shows an embodiment in which the rotor 420 has only three arms 422 and shoes 423 equally spaced at 120° intervals, and FIG. 2C shows an embodiment in which the rotor 420 has only two arms 422 and shoes 423 equally spaced at 180° intervals (i.e. diametrically opposed). It is conceivable that, in other embodiments, the rotor 420 may have only one arm 422 and an associated shoe 423, or may have more than four arms 422 and shoes 423.

The shoes or wipers 423 in the illustrated embodiments are each immovable relative to the ring member 421 of the rotor 420, so the shoes or wipers 423 slide along the inner surface of the tube 506 as the rotor 420 rotates. However, in other embodiments, some or all of the shoes 423 may be replaced by rollers that are rotatably mounted to their respective arms 422, so that the rollers rotate relative to the rotor 420 as the rotor 420 rotates relative to the compressible tube 506. Such an arrangement reduces frictional losses in the pump 400, since the rollers roll on the surface of the tube 506 as the rotor 420 rotates.

In the embodiment shown in FIG. 2A, the ring member 421 of the rotor 420 comprises an internal, or annular, gear 424 that has a circular ring of teeth 425, which teeth are all equidistantly spaced from the rotor axis R. A pinion gear 434 with teeth 435 that are meshed with the teeth 425 of the internal gear 424 also is provided.

The pinion gear 434 is mounted to the pump housing 410 for rotation about a pinion axis P relative to the pump housing 410. The pinion axis P is parallel to, offset from, and fixed relative to, the rotor axis R. Rotation of the pinion gear 434 drives rotation of the internal gear 424 relative to the compressible tube 506. The pinion gear 434 has fewer teeth than the internal gear 424, such that rotation speed of the internal gear 424 and the rotor 420 is less than rotation speed of the pinion gear 434, and such that the gears 424 and 434 act as a torque multiplier when the internal gear 424 is driven by the pinion gear 434.

Figure 3A:
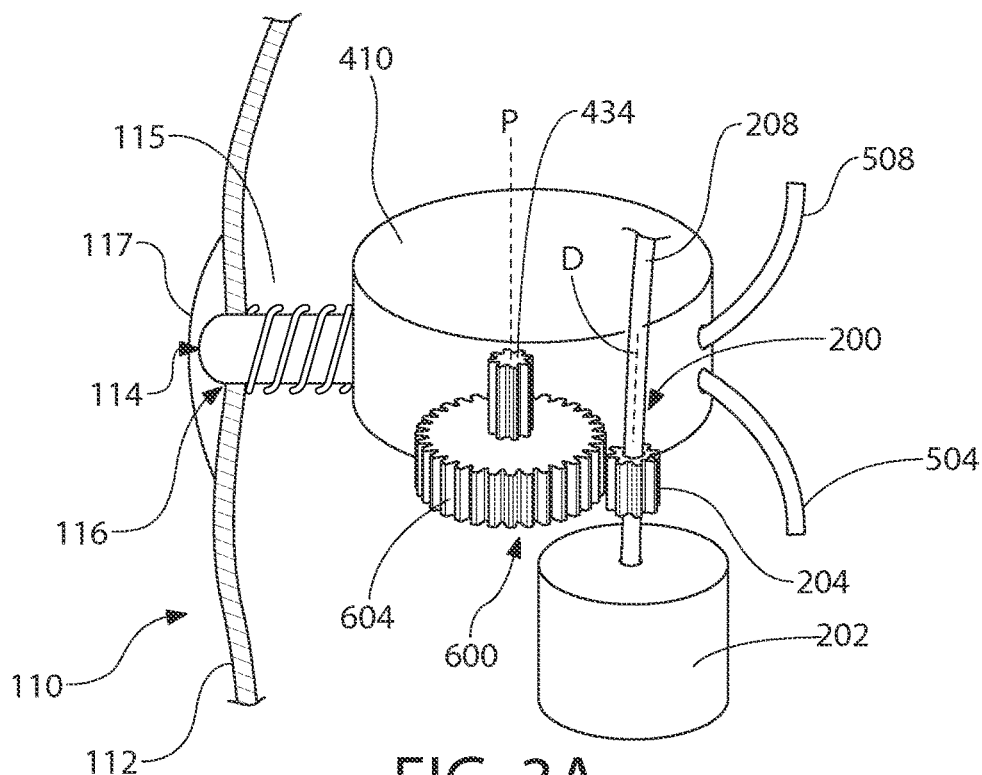
FIG. 3A is a partial perspective view of an interior of the oral care implement of the first embodiment of the present invention.

As shown in FIG. 3A, the pinion gear 434 is connected to a driving gear 604, which driving gear 604 is mounted for rotation about the same pinion axis P as the pinion gear 434. The driving gear 604 and the pinion gear 434 may be integrally formed, or one may be rotationally-fixed on an axle with which the other is integrally formed, or both may be rotationally-fixed on an axle. In any event, rotation of the driving gear 604 causes rotation of the pinion gear 434. Since the pinion axis P is fixed relative to the pump housing 410, it will be appreciated that the centre of the driving gear 604 is fixed relative to the pump housing 410.

The driving gear 604 is referred to herein as comprised in an "auxiliary device drive mechanism" 600. In this embodiment, the auxiliary device drive mechanism 600 is considered to comprise the driving gear 604 and the element (not shown) to which the driving gear 604 is connected and about which it rotates. Moreover, the driving gear 604 is referred to herein as a movable part of the auxiliary device drive mechanism 600, more particularly a rotatable part of the auxiliary device drive mechanism 600.

FIG. 3A shows the second gear 604 spaced from the first gear 204 of the carrier drive mechanism 200. That is, the first and second gears 204, 604 are disengaged from one another. Accordingly, when the toothbrush 1 is in the state illustrated in FIG. 3A, rotation of the output shaft of the motor 202 does not drive rotation of the rotor 420 via the auxiliary device drive mechanism 600. However, the auxiliary device drive mechanism 600 is selectively engagable with the carrier drive mechanism 200 during operation of the carrier drive mechanism 200 (i.e. while the drive shaft 208 and first gear 204 are rotated by the motor 202), so as to selectively operate the auxiliary device 400 while the carrier 130 is moving relative to the body 100, as will now be described in more detail.

The pump housing 410 is mounted on the housing 112 but is movable relative to the housing 112. For example, the pump housing 410 may be slidable relative to the housing 112. On the other hand, the position of the longitudinal axis D of the drive shaft 208 is fixed relative to the housing 112 and the body 100 as a whole.

As illustrated in FIGS. 1 and 3A, the toothbrush 1 comprises a selector 114 that is operable by a user to cause the second gear 604 to engage with the first gear 204, which results in the auxiliary device drive mechanism 600 being engaged with the carrier drive mechanism 200. The selector 114 is movable by a user between a first position or state, shown in FIG. 3A, and a second position or state (not shown), at which the first and second gears 204, 604 are engaged and the auxiliary device drive mechanism 600 and the carrier drive mechanism 200 are engaged. A first end of the selector 114 protrudes through a hole 116 in the housing 112 of the handle 110 from the inside of the housing 112 to the outside of the housing 112, while a second, opposite end of the selector 114 is directly or indirectly fixed to the pump housing 410 and is movable therewith relative to the housing 112. A flexible cover 117 is fixed to the outside surface of the housing 112 over the hole 116 and over the first end of the selector 114. The cover 117 prevents dust or moisture from entering the interior of the handle 110 through the hole 116.

The selector 114 is biased from its second position to its first position by a resilient element 115, which in the present embodiment comprises a coil spring, as shown in FIG. 3A. The resilient element 115 is connected between the pump housing 410 and the housing 112, biases the second gear 604 away from the first gear 204, and thus acts to bias the auxiliary device drive mechanism 600 out of engagement with the carrier drive mechanism 200.

When a user wishes to clean their teeth using the cleaning elements 134 carried by the movable carrier 130, they apply a force to the surface 201a of the switch 201, which causes the electric switch 201b to adopt its closed state. This completes the electric circuit 205, current flows through the motor 202, the output shaft of the motor 202 rotates. In turn, the drive shaft 208 moves, which drives the carrier 130 to move relative to the body 100.

When the user subsequently wishes to apply the fluid held in the reservoir 502 to their oral cavity, e.g. to their teeth or gums, they move the selector 114 from its first state to its second state against the biasing force of the resilient element 115. Since the position of the axis P of rotation of the second gear 604 is fixed relative to the pump housing 410, and since the pump housing 410 is caused to move when the selector 114 moves, movement of the selector 114 from its first to its second state causes the pump housing 410 and the second gear 604 to be moved relative to the body 100 and relative to the carrier drive mechanism 200 in a direction towards the carrier drive mechanism 200. This causes the distance between the axis D of rotation of the first gear 204 and the axis P of rotation of the second gear 604, which is parallel to the axis D of rotation of the first gear 204, to reduce until the first and second gears 204, 604 mesh. Since the first gear 204 already is rotating about its axis D of rotation, meshing of the first and second gears 204, 604 causes rotation of the second gear 604 about its axis P of rotation, and thus operation of the pump 400 to pump fluid from the reservoir 502 through the outlet(s) 510 and into the user's mouth.

When the user subsequently wishes to stop the application of fluid to their oral cavity, they release the selector 114, which returns to its first state under the biasing effect of the resilient element 115. This causes the pump housing 410 and the auxiliary device drive mechanism 600 to be moved relative to the body 100 and relative to the carrier drive mechanism 200 in a direction away from the carrier drive mechanism 200, such that the distance between the axis D of rotation of the first gear 204 and the axis P of rotation of the second gear 604 increases until the first and second gears 204, 604 disengage. Accordingly, the auxiliary device drive mechanism 600 and the carrier drive mechanism 200 become disengaged and operation of the pump 400 ceases.

In each of the embodiments shown in FIGS. 2B and 2C, the rotor 420 does not comprise an internal gear. Rather, the rotor 420 is rotatable about its axis R on an axle (not shown) that is mounted to the pump housing 410. Either a gear equivalent to the pinion gear 434 discussed above is mounted on, or integral with, the axle and engaged directly (or indirectly via other gear(s)) with a gear equivalent to the second gear 604, or the second gear 604 is itself mounted on, or integral with, the axle.

Figure 3B:
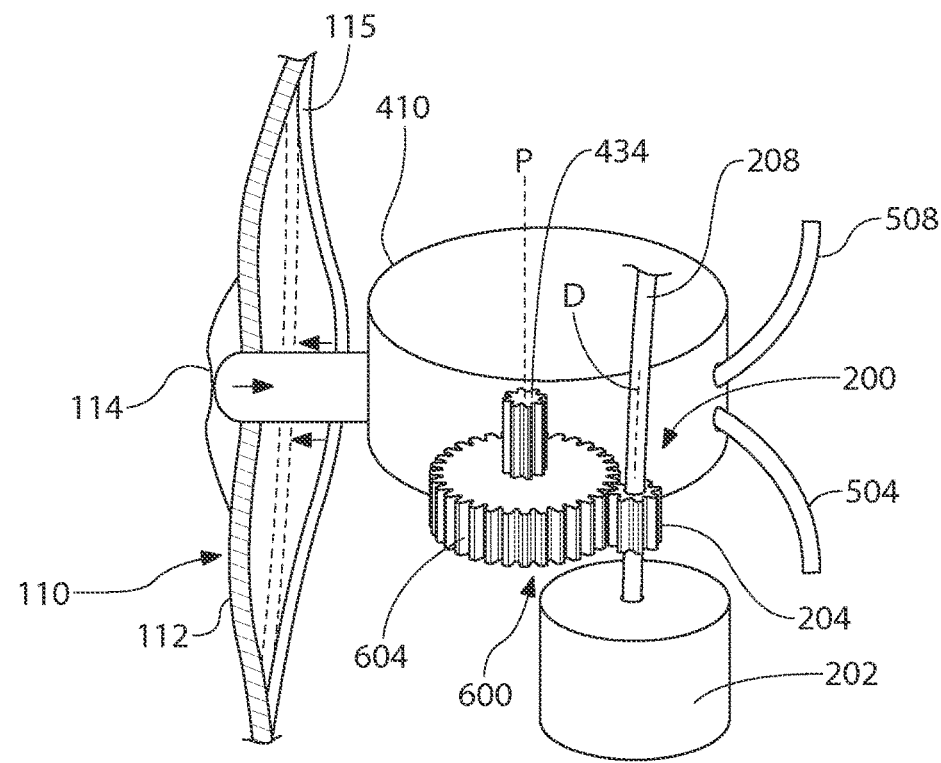
FIGS. 3B and 3C are partial perspective views of interiors of oral care implements of respective further embodiments of the present invention.

In the above described embodiment, the resilient element 115 comprises a coil spring. In alternative embodiments, the resilient element 115 may comprise a different form of spring. The resilient element may comprise an elastically-deformable membrane (such as is shown in FIG. 3B) or one or more elastically deformable beams connected between the pump housing 410 and the housing 112 of the handle 110. When the selector 114 in its second state, the membrane or beam(s) is/are deformed from a natural, equilibrium state, the first and second gears 204, 604 are meshed and thus the carrier drive mechanism 200 and the auxiliary device drive mechanism 600 are engaged. A user's subsequent release of the selector 114 allows the membrane or beam(s) to relax towards its/their equilibrium state, which is indicated by the dotted lines in FIG. 3B for the embodiment utilizing a membrane 115. It will be appreciated that such relaxation of the resilient element 115 causes the carrier drive mechanism 200 and the auxiliary device drive mechanism 600 to disengage, and thus operation of the pump to cease.

Figure 3C:
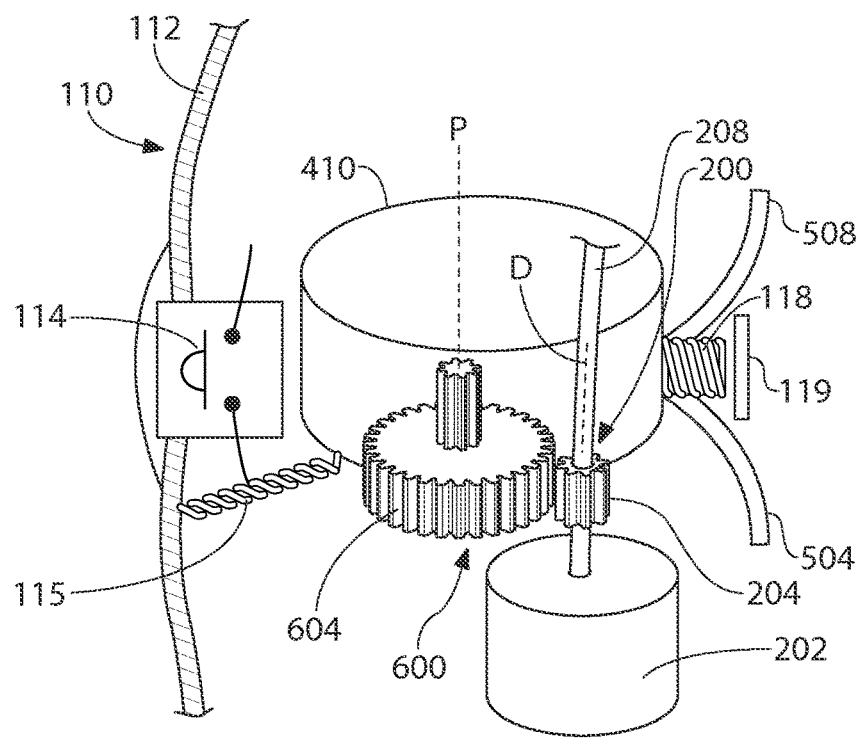

A further embodiment of the present invention is illustrated in FIG. 3C. In this embodiment, the selector 114 comprises an electrical switch that is switchable by a user (such as by pressing the switch) between a first state, in which a pump actuation electrical circuit comprising the electrical switch 114, one or more batteries and an electromagnet 118, is incomplete or open, and a second state in which the pump actuation electrical circuit is complete or closed. The battery(ies) preferably is/are the batteries 203 that is/are used to power the motor 202. The electromagnet 118 is fixed directly or indirectly to one of the housing 112 and the auxiliary device drive mechanism 600. On the other hand, a ferromagnetic element 119 is fixed directly or indirectly to the other of the housing 112 and the auxiliary device drive mechanism 600. The electromagnet 118 and ferromagnetic element 119 are relatively disposed, when the electromagnet 118 is not energized, such that subsequent energisation of the electromagnet 118 would result in relative movement between the electromagnet 118 and the ferromagnetic element 119 to cause movement of the auxiliary device drive mechanism 600 relative to the housing 112 in a direction towards the carrier drive mechanism 200.

Accordingly, as will be appreciated, when a user wishes to operate the pump 400 to expel fluid from the outlet(s) 510 during driving of movement of the carrier 130, they switch the selector 114 from its first state to its second state to close the pump actuation electrical circuit, which causes a current to flow through the electromagnet 118. This causes the relative movement between the electromagnet 118 and the ferromagnetic element 119, and thus the movement of the auxiliary device drive mechanism 600 relative to the housing 112. Given that the longitudinal axis D of the first gear 204 is fixed relative to the housing 112, this operation also causes movement of the auxiliary device drive mechanism 600 towards the carrier drive mechanism 200, which causes engagement of the first and second gears 204, 604 of the respective drive mechanisms 200, 600, and thus operation of the pump 400.

Subsequent switching of the selector 114 to its first position opens the electrical circuit and de-energises the electromagnet 118. A resilient element 115 connected between the auxiliary device drive mechanism 600 and the housing 112 biases the auxiliary device drive mechanism 600 in a direction away from the carrier drive mechanism 200 so as to increase the distance between the axes D, P of rotation of the first and second gears 204, 604 such that the first and second gears 204, 604 disengage and operation of the pump 400 ceases.

The switching of the selector 114 to its first position may be manually performed by the user. Alternatively, the electromagnet 118 may be automatically energized for a predetermined period of time, after which it is de-energised. For example, toothbrush 1 may comprise a timer (not shown) and a control circuit (not shown) that are connected to the pump actuation electrical circuit. The timer is configured to measure a predetermined period of time from a point in time at which it is estimated that the auxiliary device drive mechanism 600 and the carrier drive mechanism 200 first engage following switching of the selector 114 to its second position. This point in time may be estimated to be the point in time at which the pump actuation electrical circuit is closed, or a point in time shortly after that. The predetermined period of time is preferably between 1 and 30 seconds, more preferably between 2 and 15 seconds, and most preferably between 3 and 7 seconds. A user interface, such as a dial, may be provided via which a user is able to select the duration of the predetermined period of time.

When the timer has measured expiry of the predetermined period of time, the control circuit controls the switch 114 to move to its first state, which causes the pump actuation electrical circuit to become incomplete. In turn, this causes de-energisation of the electromagnet 118, and subsequent disengagement of the auxiliary device drive mechanism 600 from the carrier drive mechanism 200 through the above-described biasing influence of the resilient element 115.

Accordingly, the oral care implement 1 of the present invention may comprise a timer that measures a predetermined period of time from a point in time when the auxiliary device drive mechanism 600 and the carrier drive mechanism 200 become engaged, and a controller that causes disengagement of the auxiliary device drive mechanism 600 and the carrier drive mechanism 200 after the timer has determined that the predetermined period of time has expired. Alternatively, a timer and control circuit (not shown) may be may be connected to the switch 201. The timer is configured to measure a predetermined period of time from a point in time at which it is estimated that the carrier device mechanism has been activated. The point in time may be estimated to be the point in time at which the switch 201b is put into a closed state, in which the circuit 205 is complete. After expiry of the first predetermine period of time, the electromagnet 118 may be automatically energized for a second predetermined period of time, after which it is de-energized. In this embodiment, the timer controls when the auxiliary drive mechanism 600 is engaged and operating to dispense a fluid, then continues to be engaged for a second predetermined period of time, and is then automatically disengaged. Therefore the fluid dispensing is done automatically and the user doesn't need to depress anything other than the initial switch 201.

Figure 4:
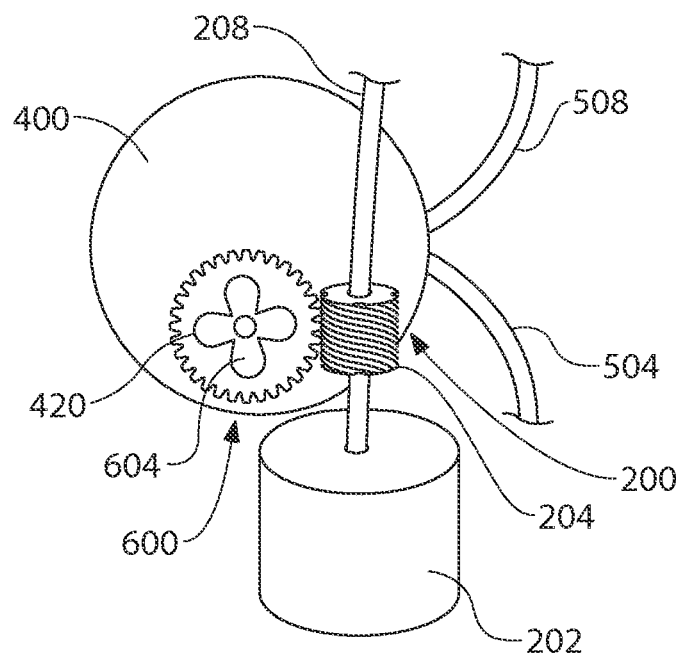
FIG. 4 is a partial perspective view of an interior of an oral care implement according to a still further embodiment of the present invention.

In each of the embodiments described above, the second gear 604 is rotatable about an axis P that is parallel to the axis D of rotation of the first gear 204. However, in alternative embodiments, these two axes P, D may be non-parallel. In some embodiments, one of the first and second gears 204, 604 may comprise an external gear and the other of the first and second gears 204, 604 may comprise a cooperating worm gear, as is shown by way of example in FIG. 4, such that these two axes P, D are perpendicular to one another. In some embodiments, both of the first and second gears 204, 604 may comprise cooperating bevel gears that are rotatable about respective non-parallel axes, such as axes that are perpendicular to one another. Other arrangements of cooperating, meshable gears that are rotatable about respective non-parallel axes will be apparent to the skilled person.

In the embodiments described above, the first and second gears 204, 604 are moved relative to one another in such a manner that a distance between their axes P, D of rotation reduces to engage the drive mechanisms 200, 600. In other embodiments, this need not be the case. For example, in some embodiments, the second gear 604 may be moved in a direction parallel to its axis P of rotation and parallel to the longitudinal axis D of the drive shaft 208, to mesh the second gear 604 with the first gear 204 to engage the drive mechanisms 200, 600. As such, the distance between the axes P, D of rotation remains unchanged.

In alternative embodiments, the distance between the axes P, D of rotation increases to engage the drive mechanisms 200, 600. For example, the first gear 204 may comprise an internal gear. The rotation axis of the second gear 604 may be located close to the rotation axis of the first gear 204 when the first and second gears 204, 604 disengaged. Subsequent movement of the rotation axis of the second gear 604 away from the rotation axis of the first gear 204 would cause meshing of the first and second gears 204, 604, and thus engagement of the drive mechanisms 200, 600.

In a variation to the embodiments discussed above, the gear 204 on the drive shaft 208 may not be the gear that the second gear 604 engages and disengages. For example, the gear 204 on the drive shaft 208 may be engaged permanently with a third gear (not shown) that is part of the carrier drive mechanism 200 and that is caused to rotate by the carrier drive mechanism 200. In such a case, it may be with this third gear that the second gear 604 of the auxiliary device drive mechanism 600 engages and disengages to engage and disengage the drive mechanisms 200, 600.

Similarly, in some embodiments the gear 604 mounted for rotation about the same axis P as the pinion gear 434 may not be the gear with which the gear of the carrier drive mechanism engages and disengages. For example, the gear 604 may permanently be engaged with another gear (not shown), and it is with this other gear that a gear of the carrier drive mechanism 200 (whether or not the gear 204 mounted on the drive shaft 208) engages and disengages.

Indeed, any number of gears may be provided as a breakable gear train configured to selectively transmit movement of the carrier drive mechanism 200 to the auxiliary device 400. That is, the auxiliary device drive mechanism 600 may comprise a first train of gears indirectly connected to the auxiliary device 400 and the carrier drive mechanism 200 may comprise a second train of gears indirectly connected to the motor 202, and one or more of the first train of gears may be configured to selectively engage and disengage one or more of the second train of gears, in order to selectively operate the auxiliary device during operation of the motor 202.

In all of the above described embodiments, the first and second rotatable parts of the carrier drive mechanism 200 and the auxiliary device drive mechanism 600 are respective engagable first and second gears 204, 604, respectively. However, the present invention is not limited to the employment of engagable first and second rotatable parts that are necessarily gears. For example, in some embodiments, the first and second engagable rotatable parts may comprise respective wheels with surfaces that may be engaged with one another and subsequently disengaged, in order to selectively transmit rotation of the first rotatable part to the second rotatable part. The surfaces would have respective coefficients of friction sufficient such that, when the surfaces of the wheels are brought into engagement, driven rotation of the first rotatable part of the carrier drive mechanism 200 is transmitted at least partially to the second rotatable part of the auxiliary device drive mechanism 600, to a degree sufficient to operate the pump or other provided auxiliary device 400. The surfaces may be respective circumferential surfaces of the first and second rotatable parts, respective axial end faces of the first and second rotatable parts, or a circumferential surface of one of the rotatable parts and an axial end face of the other of the first and second rotatable parts.

In all of the above described embodiments, the first and second movable parts of the carrier drive mechanism 200 and the auxiliary device drive mechanism 600 are respective engagable first and second rotatable parts, respectively. However, the present invention is not limited to the employment of engagable first and second movable parts that are necessarily both rotatable. For example, in some embodiments, one of the first and second engagable movable parts comprises a rack, and the other of the first and second engagable movable parts comprises a pinion that is selectively engaged with the rack. In such embodiments, the pinion may be moved in a direction parallel to, or perpendicular to, its axis of rotation in order to engage and disengage the rack.

The rack may be mounted on the drive element 208, in which case the drive element 208 may be driven by the motor 202 in an axial direction along the longitudinal axis D of the drive element 208. For example, the first end of the drive element 208 may be connected to the output shaft of the motor 202 via a suitable first linkage, such as a cam-and-follower arrangement, such that rotation of the output shaft of the motor 202 is translated into back-and-forth axial movement of the drive shaft 208. The second end of the drive element 208 is connected to the carrier 130 via a suitable second linkage to convert the back-and-forth axial movement of the drive element 208 into movement of the carrier 130. If the carrier 130 is rotatable relative to the support 122, the second linkage may comprise a cam-and-follower arrangement disposed, such that back-and-forth axial movement of the drive element 208 is translated into rotation of the carrier 130. Alternatively, if the carrier 130 is moveable linearly in a direction parallel to the longitudinal axis D of the drive element 208, the carrier 130 may be fixed directly or indirectly to the drive element 208, such that the carrier 130 follows the back-and-forth axial movement of the drive element 208.

In an alternative embodiment, the rack may be part of the auxiliary device drive mechanism 600, and the pinion is mounted on, or integral with the drive element 208, and the drive element 208 may be rotatable about its longitudinal axis D.

In a variation to these embodiments, the rack is replaced by a flat surface and the pinion is replaced by a wheel with a circumferential surface. The surfaces would have respective coefficients of friction sufficient to transmit movement between the flat surface and the wheel. The flat surface and the circumferential surface may be selectively engaged with one another and subsequently disengaged, in order to selectively transmit linear movement of the flat surface to the wheel or vice versa, depending on which of the two drive mechanisms 200, 600 each of the surfaces belongs to.

In other embodiments, one of the first and second movable parts may be a rotatable element, such as a pulley or a wheel, and the other of the first and second movable parts may be an elongate flexible element, such as belt chain, cable or wire, that is selectively engagable with the rotatable element. For example, in the embodiment shown in FIG. 3D, the auxiliary device drive mechanism 600 comprises a pulley 606 and a belt 608. The carrier drive mechanism 200 comprises a drive pulley 206 mounted on, or integral with, the drive shaft 208. The drive pulley 206 rotates with the drive shaft 208. The belt 608 initially is loose fitting on the pulley 206, 606. That is, when the auxiliary device drive mechanism 600 and the carrier drive mechanism 200 are disengaged, the belt is not engaged with one or both of the drive pulley 206 and the pulley 606. Subsequent relative movement of the drive pulley 206 and the pulley 606 in a manner such that a distance between the drive pulley 206 and the pulley 606 increases until the belt 608 is engaged with both of the pulleys 206, 606 results in engagement of the two drive mechanisms 200, 600. The movement may comprise movement of the axis of rotation of one of the drive pulley 206 and the pulley 606 relative to the housing 112, while the axis of rotation of the other of the drive pulley 206 and the pulley 606 remains fixed relative to the housing 112. Alternatively, the movement may comprise movement of the axes of rotation of both of the pulleys 206, 606 relative to the housing 112.

Figure 3D:
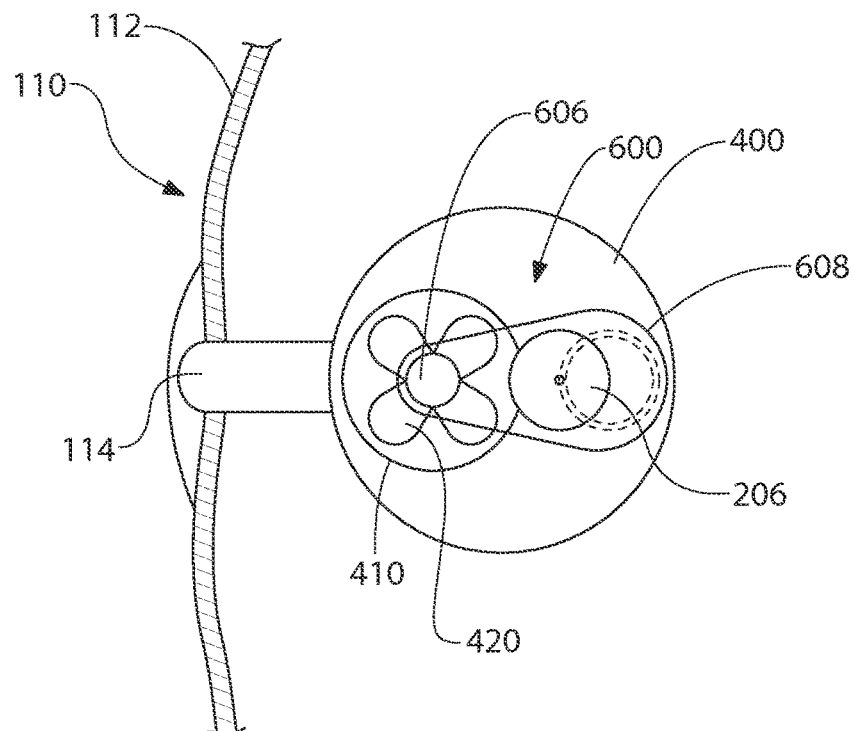
FIG. 3D is a lateral cross sectional view of part of an oral care implement according to another alternative embodiment of the present invention.

In a variation to the embodiment illustrated in FIG. 3D, the pulleys may be replaced with respective toothed wheels and the elongate flexible element comprises a chain with links that are engagable with the teeth of the toothed wheels.

In still further embodiments of the present invention, neither of the respective first and second movable parts of the carrier drive mechanism 200 and the auxiliary device drive mechanism 600 are rotatable parts. For example, in respective variations to each of the above described embodiments, the drive element 208 may be driven back-and-forth by the motor 202 in axial directions along its longitudinal axis D, in a manner similar to that described above. The drive element 208 comprises a male or female first moveable element that follows the motion of the drive element 208. The auxiliary device drive mechanism 600 comprises a female or male second moveable element that is selectively engagable with the first moveable element to engage the two drive mechanisms 200, 600. When the first and second moveable elements are engaged, the second moveable element is moved back-and-forth along a linear path by the back-and-forth axial movement of the first moveable element parallel to the longitudinal axis D of the drive element 208.

In all of the above-described embodiments, the movement of the second moveable element of the auxiliary device drive mechanism 600, as driven by the first moveable element of the carrier drive mechanism 200, is translated within the auxiliary device drive mechanism 600 into movement suitable to drive the auxiliary device 400, such as a pump.

In each of the above-described embodiments, the drive element 208 comprises a single substantially linear elongate element. In respective variations to each of the embodiments, the drive element 208 may instead comprise one or more elements, each of which may be linear or nonlinear, that link the output shaft of the motor 202 to the carrier 130. The form of the drive element 208 is not to be considered limited to any of the forms discussed above, unless otherwise stated in the claims.

In each of the above-described embodiments, at least part of the auxiliary drive mechanism 600 is moved relative to the housing 112 and relative to the carrier drive mechanism 200 in order to engage and disengage the two drive mechanisms 200, 600. In respective variations to each of the above-described embodiments, the carrier drive mechanism 200 may instead or additionally move relative to the housing 112 in order to engage and disengage the two drive mechanisms 200, 600.

In many of the above-described embodiments, the pump housing 410 is moved relative to the housing 112 and relative to the carrier drive mechanism 200 in order to engage and disengage the two drive mechanisms 200, 600. In respective variations to those embodiments, the pump housing 410 may instead be fixed relative to the housing 112, and either of both of (a) at least part of the carrier drive mechanism 200 and (b) at least part of the auxiliary device drive mechanism 600 may be moved relative to the housing 112 in order to engage and disengage the two drive mechanisms 200, 600, In those respective variations, the second end of the selector 114 may be connected to one of the drive mechanisms 200, 600 that is configured to move relative to the housing 112 during engagement/disengagement of the drive mechanisms 200, 600, rather than to the pump housing 410.

For example, in a first variation to the embodiment of FIGS. 1 and 3A, the pump housing 410 and the longitudinal axis D of the drive element 208 are fixed relative to the housing 112. The auxiliary device drive mechanism 600 comprises the gear 604 and another gear (not shown). The another gear has an axis of rotation that is moveable relative to the gear 604 in an arc about the axis P of rotation of the gear 604 while maintaining meshing of the teeth of the another gear and the gear 604. Through this movement of the axis of rotation of the another gear, the another gear is engagable and disengagable with the first gear 204 on the drive element 208.

In a second variation to the embodiment of FIGS. 1 and 3A, the pump housing 410 is fixed relative to the housing 112 (such that the rotor axis A is fixed in position relative to the housing 112), and the carrier drive mechanism 200 comprises the gear 204 and another gear (not shown). The another gear has an axis of rotation that is moveable relative to the gear 204 in an arc about the axis D of rotation of the gear 204 while maintaining meshing of the teeth of the another gear and the gear 204. Through this movement of the axis of rotation of the another gear, the another gear is engagable and disengagable with the gear 604 of the auxiliary device drive mechanism 600.

In each of these two variations, the selector 114 is connected to the axis of the another gear and is biased by a resilient element 115 to its first position, such that the drive mechanisms 200, 600 are biased to a relative position at which they are disengaged.

In each of the above-described embodiments, the rotor 420 of the pump 400 is rotatable about an axis R that is parallel to the longitudinal axis L of the implement 1. In alternative embodiments, such as that shown in FIG. 4, the rotor 420 is rotatable about an axis that is nonparallel, such as perpendicular, to the longitudinal axis L of the implement 1. In such alternative embodiments, the rotor 420 may take any of the forms described herein, for example any of those shown in FIGS. 2A to 2C.

In each of the above-described embodiments, the auxiliary device 400 comprises a pump. In respective variations to each of those embodiments, the auxiliary device does not comprise a pump. Preferably the auxiliary device is a mechanically drivable device. The auxiliary device could comprise, for example, a soft tissue massaging element or an element that causes vibration of the head 120.

In each of the above embodiments, the head 120 is integrally formed with the handle 110. In respective variations to each of the above embodiments, the head 120 may instead be detachably connected to the handle 110. In such alternative embodiments, the invention provides a kit of parts for an oral care implement 1, which kit of parts comprises a handle 110 and one or more heads 120 that is/are connectable, preferably detachably, to the handle 110. The neck 140 may be integrally formed with the head 120 and removable from the handle 110 together with the head 120. Alternatively, the neck 140 may be integrally formed with the handle 110, and the head 120 is removable from both the neck 140 and the handle 110.

The kit of parts may comprise one or more reservoirs 502, which are connectable to the first channel portion 504 of the fluid transport system 500, and which are packaged and provided to a user or consumer outside of the handle 110. The one or more reservoirs 502 may each contain fluids of the same or different compositions.

In each of the above-described embodiments, the carrier drive mechanism 200 is permanently connected to the carrier 130 and operable to drive movement of the carrier 130 relative to the body 100. In respective variations to each of the embodiments, the carrier drive mechanism 200 may instead be selectively connectable and disconnectable to the carrier 130 and operable, when connected to the carrier, to drive movement of the carrier 130 relative to the body 100.

In each of the above-described embodiments, the carrier drive mechanism 200 and the auxiliary device drive mechanism 600 are selectively engagable with one another. In respective variations to each of the described embodiments, the drive mechanisms 200, 600 may instead be permanently engaged to one another, such that the motor 202, when electrically connected to the battery(ies) 203, always drives movement of the carrier 130 and operation of the auxiliary device 400. In such scenarios, when the auxiliary device 400 comprises a rotary peristaltic pump, the axis of rotation of the rotor 420 preferably is fixed in position relative to the housing 112 and the body 100 generally.

In an alternative embodiment of the present invention, the oral care implement 1 comprises a body 100, one or more outlets 510 being formed in a surface of the body 100, and preferably in a surface of a head 120 of the body 100. Disposed within the body 100, and preferably within a handle 110 of the body 100, are a rotary peristaltic pump 400 and a fluid flow channel 506, 508 that links the pump 400 to the one or more outlets 510, in much the same way as discussed above. As discussed above, the pump 400 is operable to pump fluid to the one or more outlets 510 via the fluid flow channel 506, 508. Preferably the fluid is pumped from a reservoir 502 disposed within the handle 110, as discussed above. The fluid flow channel comprises a compressible tube 506, and the pump 400 comprises a rotor 420 and a pump housing 410, a first portion of the compressible tube 506 being compressed between the rotor 420 and the housing 410, as discussed above. The rotor 420 is rotatable about an axis R that is in a fixed position relative to the handle 110 and relative to the body 100 as a whole.

In a still further embodiment of the present invention, there is provided a kit of parts for an oral care implement, the kit of parts comprising: a handle 110; and a head 120 connectable to the handle 110, wherein the head 120 comprises one or more cleaning elements 134 and a first fluid flow channel 508, wherein one or more outlets 510 are formed in a surface of the head 120, and the first fluid flow channel 508 is in fluid communication with the one or more outlets. The handle 110 comprises a housing 112, within which are disposed a rotary peristaltic pump 400 and a second fluid flow channel 506 that engages the first fluid flow channel 508 when the head 120 is connected to the handle 110 so as to link the pump 400 to the one or more outlets 510 when the head 120 is connected to the handle 110. The pump 400 is operable to pump fluid to the one or more outlets 510 via the first and second fluid flow channels 506, 508. As discussed above, the second fluid flow channel comprises a compressible tube 506, and the pump 400 comprises a rotor 420 and a pump housing 410, wherein a first portion of the compressible tube 506 is compressed between the rotor 420 and the housing 410. The rotor 420 is rotatable about an axis R that is in a fixed position relative to the housing 112 of the handle 110.

Other modifications to the described embodiments will be apparent to those skilled in the art and are within the scope of the invention, as defined by the appended claims.

What is claimed is:

1. An oral care implement, comprising:
a body;
a carrier connected to the body and movable relative to the body, the carrier carrying one or more cleaning elements;
a carrier drive mechanism operable to drive movement of the carrier relative to the body;
an auxiliary device comprising a pump;
an auxiliary device drive mechanism that is selectively engagable with the carrier drive mechanism during operation of the carrier drive mechanism, so as to selectively operate the auxiliary device during movement of the carrier relative to the body;
a timer configured to measure a predetermined period of time from engagement of the auxiliary device drive mechanism with the carrier drive mechanism; and
wherein the implement is configured such that, when the timer has measured elapse of the predetermined period of time, the auxiliary device drive mechanism is disengaged from the carrier drive mechanism.

2. The oral care implement of claim 1, wherein the auxiliary device drive mechanism is selectively engagable with the carrier drive mechanism through relative movement of at least part of the auxiliary device drive mechanism and at least part of the carrier drive mechanism.

3. The oral care implement of claim 2, wherein the auxiliary device drive mechanism is selectively engagable with the carrier drive mechanism through movement of at least part of the auxiliary device drive mechanism relative to the body and relative to at least part of the carrier drive mechanism.

4. The oral care implement of claim 1, wherein the carrier drive mechanism comprises a first movable part and the auxiliary device drive mechanism comprises a second movable part,
wherein the operation of the carrier drive mechanism causes movement of the first movable part, and
wherein the second moveable part is selectively engagable with the first movable part during the movement of the first movable part.

5. The oral care implement of claim 4, wherein the first movable part is a first rotatable part and the movement of the first movable part comprises rotation of the first rotatable part.

6. The oral care implement of claim 5, wherein the second movable part is a second rotatable part, wherein the first rotatable part is rotatable about a first axis and the second rotatable part is rotatable about a second axis.

7. The oral care implement of claim 5, wherein one of the first movable part and the second movable part comprises a rotatable element and the other of the first movable part and the second movable part comprises an elongate flexible element.

8. The oral care implement of claim 7, wherein the rotatable element comprises one of a pulley and a toothed wheel, and the elongate flexible element comprises one of a belt, a chain, a wire and a cable.

9. The oral care implement of claim 1, wherein the auxiliary device drive mechanism is biased out of engagement with the carrier drive mechanism.

10. The oral care implement of claim 1, comprising a selector that is operable by a user to cause the auxiliary device drive mechanism to engage with the carrier drive mechanism.

11. The oral care implement of claim 10, wherein the selector is movable between first and second positions and is biased to the first position, and
wherein, when the selector is in the first position, the auxiliary device drive mechanism is disengaged from the carrier drive mechanism, and, when the selector is in the second position, the auxiliary device drive mechanism is engaged with the carrier drive mechanism.

12. The oral care implement of claim 1, wherein the pump comprises a peristaltic pump.

13. The oral care implement of claim 12, comprising a reservoir for holding a fluid, one or more outlets formed in a surface of the body, and a fluid flow channel that links the reservoir to the one or more outlets, wherein the pump is operable to pump fluid from the reservoir to the one or more outlets via the fluid flow channel.

14. The oral care implement of claim 13, wherein the fluid flow channel comprises a compressible tube, a first portion of the tube being compressed between two components of the peristaltic pump,
wherein operation of the peristaltic pump comprises movement of at least one of the two components relative to the first portion of the tube, such that compression of the first portion of the tube is relaxed and such that a second, different portion of the tube, which second portion is closer than the first portion of the tube to the one or more outlets, becomes compressed between two components, whereby fluid is pumpable along the tube towards the one or more outlets.

15. The oral care implement of claim 14, wherein the peristaltic pump comprises a rotary peristaltic pump in which at least one of the two components is rotatable about an axis.

16. The oral care implement of claim 13, wherein the carrier drive mechanism comprises a motor and one or more elements coupling the motor to the carrier, wherein rotation of an output shaft of the motor drives movement of the carrier relative to the body.

17. The oral care implement of claim 16, comprising one or more batteries electrically connected to the motor, wherein the body comprises a housing and wherein the reservoir is located in a space between an outer wall of the housing and one of the one or more batteries.

18. An oral care implement comprising;
a body;
a carrier connected to the body and movable relative to the body, the carrier carrying one or more cleaning elements;
a carrier drive mechanism operable to drive movement of the carrier relative to the body;
an auxiliary device comprising a pump;
an auxiliary device drive mechanism that is selectively engagable with the carrier drive mechanism during operation of the carrier drive mechanism so as to selectively operate the auxiliary device during movement of the carrier relative to the body;
wherein the carrier drive mechanism comprises a first rotatable part and the auxiliary device drive mechanism comprises a second rotatable part;
wherein the operation of the carrier drive mechanism causes rotation of the first rotatable part about a first axis;
wherein the second rotatable part is selectively engagable with the first rotatable part during the rotation of the first rotatable part, the second rotatable part being rotatable about a second axis; and
wherein the second rotatable part is selectively engagable with the first rotatable part by changing a distance between the first axis and the second axis.

19. The oral care implement of claim 18, wherein the second rotatable part is selectively engagable with the first rotatable part by reducing a distance between the first axis and the second axis.

20. The oral care implement of claim 18, wherein the first axis is parallel to the second axis.

21. The oral care implement of claim 18, wherein the first axis is non-parallel to the second axis.

22. An oral care implement comprising:
a body;
a carrier connected to the body and movable relative to the body, the carrier carrying one or more cleaning elements;
a carrier drive mechanism operable to drive movement of the carrier relative to the body;
an auxiliary device comprising a pump;
an auxiliary device drive mechanism that is selectively engagable with the carrier drive mechanism during operation of the carrier drive mechanism so as to selectively operate the auxiliary device during movement of the carrier relative to the body;
wherein the carrier drive mechanism comprises a first rotatable part and the auxiliary device drive mechanism comprises a second rotatable part;
wherein the operation of the carrier drive mechanism causes rotation of the first rotatable part about a first axis;
wherein the second rotatable part is selectively engagable with the first rotatable part during the rotation of the first rotatable part, the second rotatable part being rotatable about a second axis; and
wherein the first and second axes are coaxial, and the first rotatable part is selectively engagable with the second rotatable part by changing a distance between the first and second rotatable parts in a direction parallel to the axes.

23. An oral care implement comprising:
a body;
a carrier connected to the body and movable relative to the body, the carrier carrying one or more cleaning elements;
a carrier drive mechanism operable to drive movement of the carrier relative to the body;
an auxiliary device comprising a pump;
an auxiliary device drive mechanism that is selectively engagable with the carrier drive mechanism during operation of the carrier drive mechanism so as to selectively operate the auxiliary device during movement of the carrier relative to the body;
wherein the carrier drive mechanism comprises a first rotatable part and the auxiliary device drive mechanism comprises a second rotatable part;
wherein the operation of the carrier drive mechanism causes rotation of the first rotatable part about a first axis;
wherein the second rotatable part is selectively engagable with the first rotatable part during the rotation of the first rotatable part, the second rotatable part being rotatable about a second axis; and
wherein the first rotatable part comprises a first gear and the second rotatable part comprises a second gear.

24. An oral care implement comprising:
a body;
a carrier connected to the body and movable relative to the body, the carrier carrying one or more cleaning elements;
a carrier drive mechanism operable to drive movement of the carrier relative to the body;
an auxiliary device comprising a pump;
an auxiliary device drive mechanism that is selectively engagable with the carrier drive mechanism during operation of the carrier drive mechanism, so as to selectively operate the auxiliary device during movement of the carrier relative to the body; and
an electromagnet and a ferromagnetic member, wherein when the electromagnet is energized, the electromagnet and the ferromagnetic member move relative to one another to cause the auxiliary device drive mechanism to engage with the carrier drive mechanism.

25. The oral care implement of claim 24, comprising a timer configured to measure a first predetermined period of time from the start of operation of the carrier drive mechanism and a second predetermined period of time, wherein the implement is configured such that, when the timer has measured elapse of the first predetermined period of time, the auxiliary device drive mechanism is engaged with the carrier drive mechanism and when the timer has measured elapse of the second predetermined period of time, the auxiliary device drive mechanism is disengaged from the carrier drive mechanism.

* * * * *